(12) United States Patent
Gehrig

(10) Patent No.: US 8,981,797 B2
(45) Date of Patent: Mar. 17, 2015

(54) DETERMINING A DIELECTRIC PROPERTY OF A CAPACITOR

(75) Inventor: Reto Gehrig, Winterhur (CH)

(73) Assignee: Uster Technologies, AG, Uster (CH)

( * ) Notice: Subject to any disclaimer, the term of this patent is extended or adjusted under 35 U.S.C. 154(b) by 445 days.

(21) Appl. No.: 13/121,602

(22) PCT Filed: Oct. 12, 2009

(86) PCT No.: PCT/CH2009/000329
§ 371 (c)(1),
(2), (4) Date: Mar. 29, 2011

(87) PCT Pub. No.: WO2010/043065
PCT Pub. Date: Apr. 22, 2010

(65) Prior Publication Data
US 2011/0181304 A1    Jul. 28, 2011

(30) Foreign Application Priority Data

Oct. 16, 2008   (CH) ...................... 1646/08

(51) Int. Cl.
*G01R 27/26* (2006.01)
*B65B 13/02* (2006.01)
*B65B 13/18* (2006.01)
*B65B 13/32* (2006.01)
(Continued)

(52) U.S. Cl.
CPC ............. *B65B 13/025* (2013.01); *B65B 13/187* (2013.01); *B65B 13/322* (2013.01); *G01N 33/365* (2013.01); *G01N 27/228* (2013.01)
USPC .......................................... 324/674; 324/672

(58) Field of Classification Search
CPC .................................................. B65H 63/064
USPC .......................................... 324/674
See application file for complete search history.

(56) References Cited

U.S. PATENT DOCUMENTS 3,185,924 A  *  5/1965  Locher ........................... 324/671
3,646,434 A  *  2/1972  Norwich ........................ 324/669
3,684,953 A     8/1972  Grant
(Continued)

FOREIGN PATENT DOCUMENTS

DE     19535177     3/1997
DE     19850290     5/2000
(Continued)

*Primary Examiner* — Melissa Koval
*Assistant Examiner* — Stephen G Armstrong
(74) *Attorney, Agent, or Firm* — Luedeka Neely Group, P.C.; Rick Barnes

(57) ABSTRACT

An apparatus for determining a dielectric property of a capacitor arrangement, having an alternating signal generator for applying an electric alternating signal to the capacitor arrangement. It further contains an evaluation circuit for evaluating at least one electric measuring quantity of an electric signal tapped from the capacitor arrangement. It further comprises balancing means which are arranged in an electric path between the alternating signal generator and the capacitor arrangement and by means of which a parameter of the electric alternating signal can be changed in such a way that an output signal of the evaluation circuit assumes a specific value, preferably zero, under defined constant conditions. Control means are provided for emitting an electric control signal to the balancing means, by means of which the change of the at least one parameter can be controlled. The apparatus can thus be balanced in a simple, rapid, cost-effective and especially automatic way.

27 Claims, 5 Drawing Sheets

(51) Int. Cl.
*G01N 33/36* (2006.01)
*G01N 27/22* (2006.01)

(56) References Cited

U.S. PATENT DOCUMENTS

| | | |
|---|---|---|
| 3,684,954 A | 8/1972 | Jaggers et al. |
| 3,757,211 A | 9/1973 | Goto |
| 3,768,006 A | 10/1973 | Mueller |
| 4,706,203 A | 11/1987 | Ramsdale et al. |
| 4,772,844 A | 9/1988 | Andeen et al. |
| 4,843,879 A | 7/1989 | Enderlin |
| 6,346,819 B1 | 2/2002 | Joss |
| 6,946,852 B2 | 9/2005 | Centanni |
| 2001/0008478 A1 | 7/2001 | McIntosh |
| 2008/0084220 A1* | 4/2008 | Schroder ............... 324/658 |
| 2008/0111563 A1 | 5/2008 | Ott |

FOREIGN PATENT DOCUMENTS

| | | |
|---|---|---|
| DE | 102005006853 | 8/2006 |
| EP | 1124134 | 8/2001 |
| GB | 638365 | 6/1950 |
| GB | 963258 | 7/1964 |
| GB | 1061635 | 3/1967 |
| WO | 2004083813 | 9/2004 |
| WO | 2007115416 | 10/2007 |

* cited by examiner

DETERMINING A DIELECTRIC PROPERTY OF A CAPACITOR

FIELD

The present invention lies in the field of the electric measuring apparatuses. It relates to an apparatus and a method for determining a dielectric property of a capacitor arrangement according to the preambles of the independent claims. The invention allows automatic balancing of the apparatus, a simulation of measurements with the apparatus, a testing of the apparatus or a testing of components connected downstream with the apparatus.

A preferred field of application for the invention is the capacitive testing of elongated, preferably textile structures such as card slivers, roving yarns, yarns or fabrics. The goal of such an examination can be for example the detection of foreign substances, the recognition of changes of the mass per unit of length and/or the measurement of humidity in the test subject. The invention can be used for example in the production process (online) in yarn cleaners in spinning and bobbing winding machines or in laboratory tests (offline) in yarn testing devices.

BACKGROUND

A large number of various apparatuses are known for examining or testing elongated textile test subjects such as card slivers, roving yarns, yarns or fabrics for example. Depending on their application, they can be categorized into the two classes of laboratory test (offline) and testing during the production process (online). The apparatuses make use of the various known sensor principles, of which the capacitive measuring principle is of special interest in this case, wherein a measuring capacitor is typically designed as a planar plate capacitor and comprises a through-opening for the test subject. The measuring capacitor is part of an LC oscillator, so that an electric alternating voltage is applied to the measuring capacitor upon excitation of the LC oscillator. The through-opening is thus subjected to an alternating electrical field. The test subject is moved through the plate capacitor and is subjected to the alternating field. An electric output signal of the plate capacitor is detected. Dielectric properties of the test subject are determined from the output signal in an evaluation circuit. Changes in the parameters of the test subject such as mass per unit of length and/or material composition are determined from the dielectric properties. A capacitive yarn or sliver sensor is described for example in GB-638,365 A.

In order to enable the performance of precise measurements which are not influenced by external influences such as air temperature or air humidity, a compensation method is frequently applied. For this purpose, the apparatus comprises a reference capacitor in addition to the actual measuring capacitor. It can be formed by adding a third capacitor plate arranged parallel to the two measuring capacitor plates, with the three capacitor plates being switched together into one capacitive measuring circuit. Examples for measuring circuits and suitable evaluation circuits for their output signals can be found in the specifications EP-0'924'513 A1, WO-2006/105676 A1 and WO-2007/115416 A1.

The measuring circuit should supply an output signal of the value zero when an alternating voltage is applied without test material. Due to the various imperfections in real electric components, it is not sufficient in practice to design the measuring circuit symmetrically in order to obtain a zero signal without the test material. Each measuring circuit needs to be balanced individually for symmetrization. Symmetric balancing occurs in production by the manufacturer and optionally during maintenance by a service technician. For this purpose, the capacitance of at least one capacitance trimmer connected in parallel to the measuring circuit is usually changed. Trimming occurs manually with a suitable tool, e.g. a screwdriver. The known method of laser trimming is applied alternatively. In any case, the apparatus needs to be opened for the balancing. Such a manual balancing is laborious, time-consuming and expensive.

DE-10'2005'006'853 discloses a measurement system with a sensor element which comprises a conductor structure forming a first oscillating circuit. A second oscillating circuit is coupled with the first oscillating circuit and contains a changeable component, so that its resonant frequency is adjustable. Since the two oscillating circuits form a coupled system, the resonance behavior determined by the first oscillating circuit can be influenced and thus shifted towards desired values. As a result, deviations in the capacitive or inductive components of the conductor structure which may optionally occur during the production or mounting of the sensor elements can thus be compensated.

GB-963,258 A shows a capacitive yarn clearer with a measuring capacitor through which the yarn passes. The voltage applied to the measuring capacitor is tapped and used for triggering the yarn cut. A variable resistor is switched in series with the measuring capacitor and the ends of the series circuit thus formed are connected to an AC voltage generator. The sensitivity of the yarn clearer can be set by changing the resistance.

U.S. Pat. No. 3,768,006 A shows apparatus and method for the capacitive measurement of the water content in an oil/water emulsion which flows in a pipeline. The outside wall of the pipe forms the outer grounded electrode of the measuring capacitor and an element arranged in the middle of the pipe forms the inner electrode. A reference capacitor of known capacity is connected in series with the measuring capacitor. An AC voltage generator generates an alternating voltage which is applied to the two capacitors. The voltage via the reference capacitor is measured and is a measure for the water content. The voltage over the measuring capacitor filled with the measuring subject is kept constant with a control circuit which controls the output amplitude of the AC voltage generator.

U.S. Pat. No. 3,684,953 A deals with an apparatus and method for the quantitative determination of a property of a dielectric test subject, especially its relative humidity content. The test subject is introduced into a measuring capacitor. And electric alternating signal is applied to the measuring capacitor, which signal is generated by an oscillator with an amplifier connected in series. A signal tapped from the measuring capacitor is demodulated and is compared with the alternating signal which is also demodulated and is applied to the measuring capacitor, in that quotient of the two signals is formed. The humidity content of the test subject is derived from the comparison. In order to maintain the dynamics range of the demodulators, the amplification of the amplifier is controlled by the demodulated output signal of the measuring capacitor. A variable balancing capacitor which is connected parallel to the measuring capacitor is provided for the zero balancing without test subject.

A device for the capacitive quality control of textile threads is known from U.S. Pat. No. 4,843,879 A. It contains a double-capacitor arrangement with a measuring capacitor and a reference capacitor. The double-capacitor arrangement is built into an electric circuit. The circuit contains an oscillator for applying two alternating voltages with opposite phases to the two outer capacitor electrodes of the double-capacitor arrangement. A signal amplifier and a balancing capacitor are disposed in each branch between the oscillator and the respective electrode. The balancing capacitors are used for balancing the output signal of the double-capacitor arrangement to the value of zero without any test subject.

SUMMARY

It is therefore the object of the present invention to provide an apparatus and a method for determining at least one dielectric property of a capacitor arrangement which does not have the above disadvantages. The apparatus shall be capable of being balanced in a simple, rapid, cost-effective and especially automatic way. It is a further object of the present invention to provide a method for simulating measurements with the apparatus, for testing the apparatus or for testing components connected downstream with the apparatus.

These and other objects are achieved by the apparatus and method in accordance with the invention, as defined in the independent claims. Advantageous embodiments are disclosed in the dependent claims.

The invention is based on the idea of providing balancing means in an electric path between an alternating signal generator and a measuring circuit containing the capacitor arrangement, which are controllable by means of an electric control signal in order to balance an output signal of the apparatus. The apparatus is balanced with such external balancing means without intervening in the capacitor arrangement itself. This offers the possibility of automatic balancing of the apparatus.

The term "capacitor arrangement" shall be understood in this specification as being an arrangement with two bodies which can be charged in a non-similar manner by the electrical alternating signal of the alternating signal generator and are separated from one another by at least one dielectric. In a preferred embodiment, the capacitor arrangement concerns a capacitor with two mutually spaced plates, between which air is disposed and between which a moved elongated textile test subject can be inserted which is to be examined. The term "electrical alternating signal" shall be understood within this specification to be an electric voltage or current signal with at least one time-varying, preferably periodic, component (AC component), which can additionally be superposed by a temporally substantially constant component (DC component, offset).

The apparatus in accordance with the invention for determining at least one dielectric property of a capacitor arrangement contains at least one alternating signal generator for applying an electrical alternating signal to the capacitor arrangement. It further contains an evaluation circuit for evaluating at least one electric measuring quantity of an electric signal tapped from the capacitor arrangement. The apparatus further contains balancing means which are arranged in an electric path between the at least one alternating signal generator and the capacitor arrangement and by means of which at least one parameter of the electric alternating signal can be changed in such a way that an output signal of the evaluation circuit assumes a specific value, preferably zero, under defined constant conditions. There are control means for emitting an electric control signal to the balancing means, by means of which the change of the at least one parameter is controllable.

In a preferred embodiment, the apparatus comprises a feedback by means of which an output signal of the capacitor arrangement or the evaluation circuit acts upon the control means. The capacitor arrangement is preferably decoupled from the alternating signal generator in such a way that it does not relevantly influence the basic frequency and the signal shape of the applied alternating signal.

Various exemplary variants are proposed for realizing the balancing means, with the listing not being exhaustive:

The balancing means contain a plurality of electric resistors which can be activated or deactivated individually or in groups.

The balancing means contain a modulator for an amplitude modulation of the electric alternating signal.

The balancing means contain an amplifier with variable or programmable amplification for amplifying the electric alternating signal.

The balancing means contain a digital potentiometer or a rejustor.

The balancing means contain a variable-capacitance diode.

The balancing means contain a digital-to-analog converter for applying an electric voltage to the at least one alternating signal generator, with the at least one alternating signal generator being arranged in such a way that the at least one parameter of the electric alternating signal is variable by the application of the electric voltage.

The apparatus in accordance with the invention preferably contains a reference capacitor which is connected in series to the capacitor arrangement. The at least one alternating signal generator can be set up in such a way that two electric alternating voltages with opposite phases are applied to the capacitor arrangement or the reference capacitor. The balancing means can be arranged in the electric path between the alternating signal generator and the capacitor arrangement and/or in the electric path between the at least one alternating signal generator and the reference capacitor.

The preferred use of the apparatus in accordance with the invention is the capacitive examination of a moved elongated textile test subject such as card sliver, roving yarn, yarn or fabric, with the moved test subject influencing the capacitor arrangement.

In the method in accordance with the invention for determining at least one dielectric property of a capacitor arrangement, an electric alternating signal is generated by at least one alternating signal generator and applied to the capacitor arrangement. At least one electric measuring quantity of an electric signal tapped from the capacitor arrangement is evaluated. At least one parameter of the electric alternating signal in an electric path between the at least one alternating signal generator and the capacitor arrangement is changed in such a way that an output signal of the evaluation assumes a specific value, preferably zero, under defined constant conditions. The change of the at least one parameter is controlled by an electric control signal.

In accordance with a first preferred embodiment of the method in accordance with the invention, the capacitor arrangement is left substantially unchanged in a temporal respect, an electric alternating signal is applied to the capacitor arrangement, an electric output signal of the capacitor arrangement is tapped, and the electric control signal is influenced by the output signal. The influencing of the electric control signal by the output signal can occur automatically in a closed feedback control loop. This first embodiment of the method in accordance with the invention can be used for balancing the apparatus in accordance with the invention in such a way that the output signal assumes a specific value, preferably zero, under defined constant conditions.

In accordance with a second preferred embodiment of the method in accordance with the invention, the capacitor arrangement is left substantially unchanged in a temporal respect, and the electric control signal is independent of an output signal of the capacitor arrangement. The electric control signal can be a temporally rapidly changing, synthetically generated and/or previously stored signal. This second embodiment of the method in accordance with the invention can be used for simulating measurements with the apparatus in accordance with the invention, for testing the apparatus in accordance with the invention or for testing components connected downstream with the apparatus in accordance with the invention.

The following can be mentioned as direct advantages offered by the invention:

Firstly, the balancing need not occur in the measuring circuit. The measuring circuit is the most sensitive part of the capacitive apparatus and is thus exceptionally sensitive to disturbances and nonlinearities. By arranging the balancing means outside of the measuring circuit, the invention avoids such disturbances in the measuring circuit.

Secondly, the balancing in accordance with the invention can occur with any precision. A digital potentiometer can be used for example whose resistance can be controlled via an interface with a resolution of arbitrary size.

Thirdly, the invention is capable of considerably improving the signal-to-noise ratio for all capacitive sensors in which the balancing has so far occurred by a trimmable capacitor in the measuring circuit. This is because a trimmable element in the measuring circuit will have a permanent effect on the measuring circuit.

The invention is useful for balancing the apparatus. The balancing of the apparatus can occur in a simple, rapid and cost-effective way thanks to the invention. The device no longer needs to be opened in order to balance the measuring circuit. The balancing can be made at any time. It can automatically be made by the device itself without any intervention by an operator. This allows performing the balancing at any time. A balancing could be performed before each measurement with the measuring circuit, before every $10^{th}$ measurement, or automatically after relevant changes of long-term properties of the output signal or after a larger change of the environmental conditions. This can lead to an increase in the precision, reliability and reproducibility of the measurement, and generally to an improvement in the results of the measurement.

The balancing means can be useful not only for the balancing of the measuring circuit. They can also be used for feeding arbitrary electric control signals to the apparatus. The apparatus is detuned in a purposeful manner by means of such control signals. A purposeful detuning of the apparatus can have the same or similar effect as a detuning by a change in the capacitance to be measured. Measurements can be simulated by feeding control signals to the apparatus via the balancing means. The capacitances of the apparatus should not change in this process, with the exception of the balancing means. Simulated measurements can be used for testing an evaluation circuit and for error searches in the evaluation circuit for example. They can be used for a balancing of the evaluation circuit, e.g. of filters contained in the evaluation circuit. They can also be used for testing and/or setting the apparatus. It is possible to record the preceding output signals of real measurements with the same apparatus or another sensor, store them in a memory and supply them as input signals via the variable capacitance to the apparatus. The apparatus can thus be provided with a "record and playback" function.

BRIEF DESCRIPTION OF THE DRAWINGS

The invention is explained below in closer detail by reference to the schematic drawings.

DETAILED DESCRIPTION

Figure 1:
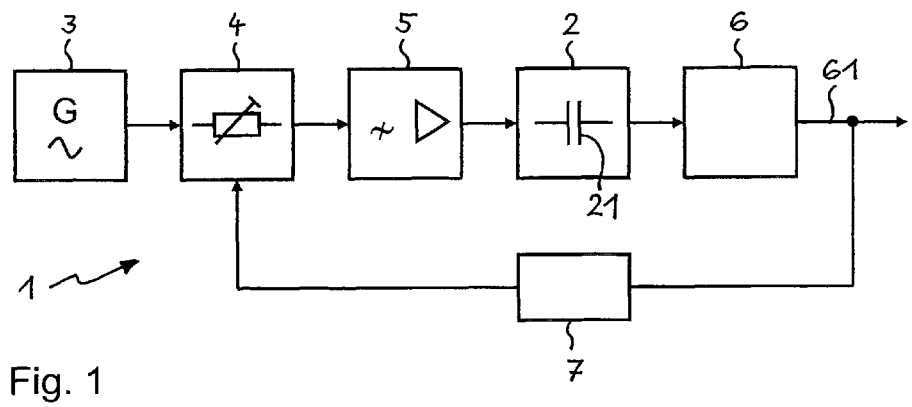
FIG. 1 shows a block diagram of the apparatus in accordance with the invention.

FIG. 1 explains the invention on the basis of a simple block diagram. The apparatus 1 in accordance with the invention is used for measuring a capacitor 21 which can be inserted in a measuring circuit 2. An electric alternating signal such as an alternating voltage is applied to the measuring circuit 2. An alternating signal generator 3 is provided for generating the alternating signal. The alternating signal generated by the alternating signal generator 3 can be filtered and/or amplified in a filter and/or amplifier stage 5. The filter and/or amplifier stage 5 is preferably also used to decouple the capacitor 21 to be measured from the alternating signal generator 3 in such a way that it does not influence parameters of the alternating signal generated by the alternating signal generator 3, e.g. frequency, phase and/or amplitude of the alternating signal. For the sake of simplicity, the filter and/or amplifier stage 5 is no longer shown in the following drawings. The measuring circuit 2 is preferably provided with an evaluation circuit 6 which is connected downstream and which evaluates an output signal of the measuring circuit 2. The evaluation circuit 6 can be arranged as a computer. It outputs an output signal on an output line 61, which output signal is a measure for the capacitor 21 to be measured. It is understood that further stages can be provided in the apparatus 1 in accordance with the invention. It can especially be advantageous or necessary to include amplifiers and/or mixers between the measuring circuit 2 and the evaluation circuit 6, which amplifiers and mixers are not shown in the enclosed drawings for reasons of simplicity of the illustration.

In accordance with the invention, balancing means 4 for balancing the apparatus 1 are arranged in an electric path between the alternating signal generator 3 and the measuring circuit 2, by means of which at least one parameter, e.g. the amplitude, of the electric alternating signal can be changed. During the balancing of the apparatus 1 it should be ensured that the capacitor 21 to be measured and optionally other capacitors present in the apparatus 1 do not change over time. Time-constant ambient conditions such as temperature and air humidity should prevail, or respective changes should be compensated. If the capacitor 21 to be measured is arranged as a capacitor for accommodating the test subject (as will be shown in the drawings below), no test subject should be present in the capacitor, or the capacitance of the test subject should not change over time. An electric alternating signal is applied to the capacitor 21 to be measured for the purpose of balancing the apparatus 1. The balancing means 4 change at least one parameter of the electric alternating signal in such a way that the output signal of the apparatus 1 on the output line 61 assumes a specific value, and preferably becomes zero. For this purpose, the balancing means 4 can be set manually by a person, e.g. after the production or during maintenance of the apparatus 1. Alternatively, the balancing means 4 can be set automatically. The automatic setting can be performed in a specially provided control unit 7 or in the evaluation unit 6. FIG. 1 shows the feedback from the output line 61 to the balancing means 4, which feedback sends a control signal dependent on the evaluation unit 6 or the measuring circuit 1 to the balancing means 4. The apparatus 1 can be balanced automatically with an automatic setting of the balancing means 4. In this way there is a closed feedback control loop, in which the output signal is the control quantity that is to be controlled to the setpoint value of zero, the control unit 7 acts as a controller and the control signal is the actuating value. Alternatively, the control quantity can be tapped upstream instead of downstream the evaluation unit 6.

Figure 2:
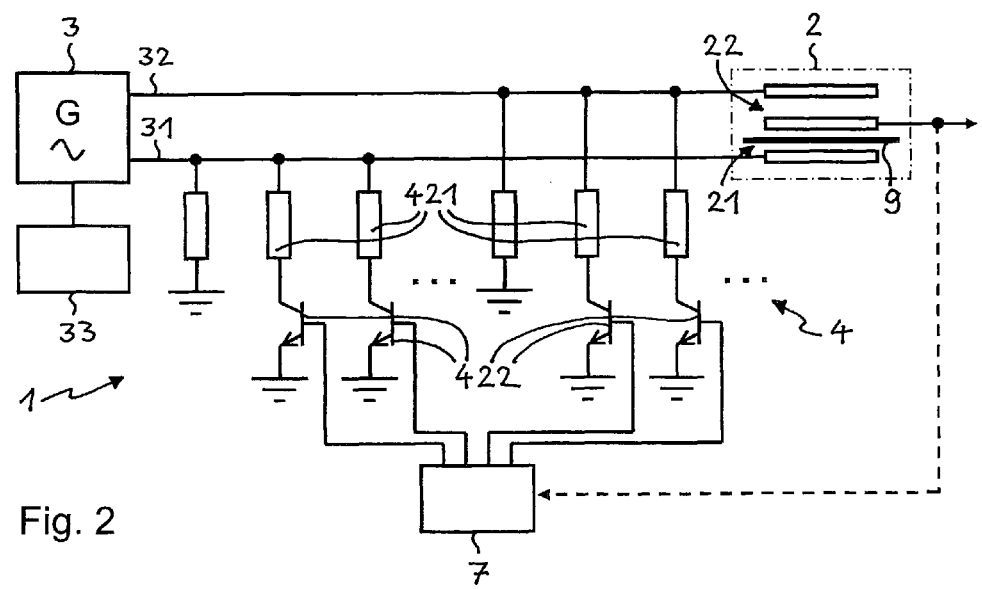
FIGS. 2 to 9 show circuit diagrams of different embodiments of the apparatus in accordance with the invention.

A first embodiment of the apparatus 1 in accordance with the invention is shown in FIG. 2. The apparatus 1 is used for capacitive measurement of a test subject 9, e.g. a yarn. For this purpose, the test subject 9 is introduced into a measuring capacitor 21, e.g. a planar plate capacitor. The measuring capacitor 21 forms a capacitive measuring circuit 2 together with a series-connected reference capacitor 22 and possibly further components (not shown). An evaluation unit 6 can be connected downstream with the measuring circuit 2, as shown in FIG. 1, which evaluation circuit is not shown in FIG. 2 and the following drawings for reasons of clarity of the illustration.

The alternating signal generator 3 can be for example a synthesizer, preferably a direct digital synthesizer (DDS). The synthesizer 3 can be triggered by a digital interface 33. The synthesizer 3 preferably comprises two outputs 31, 32 for two electric alternating signals which are substantially identical, but are phase-shifted by 180° against one another. The person skilled in the art also knows other alternating signal generators which are suitable for applying an electric alternating signal to the measuring circuit 2, e.g. from the following set: RC oscillator, LC oscillator, quartz oscillator, oscillator with ceramic resonator, oscillator with SAW component (surface acoustic waves, SAW), oscillator with logic units, synthesizer, phase-locked loop (PLL), pulse-width modulator (PWM), trigger circuit.

In the embodiment of FIG. 2, the balancing means 4 comprise a plurality of resistors 421 which are connected in parallel with respect to each other and which can be activated and deactivated individually or in groups by switches 422, e.g. high-frequency transistors. This leads to a variable overall resistance, via which a voltage drops accordingly and which further depends on the current emitted by the synthesizer. The resistors 421 can be attached to only one of the two synthesizer outputs or, as shown in the embodiment of FIG. 1, to both synthesizer outputs 31, 32. The switches 422 can be controlled by a respective digital interface 7.

For the purpose of automatic balancing of the apparatus 1, a feedback can be provided between the output signal of measuring circuit 2 and the digital interface 7 which triggers the switches 422. In order to balance the apparatus, no test subject 9 is introduced into the measuring capacitor in a preferred application and notice is taken that the ambient conditions such as air humidity and temperature are as constant as possible over time. An electric alternating signal is applied to the measuring circuit 2 by means of the synthesizer 3, and the positions of the switches 422 are controlled by the digital interface 7 in such a way that the output signal of the measuring circuit 2 is zero. If this is the case, apparatus 1 is balanced and the positions of the switches 422 are stored and maintained for the actual measurements with the test subject 9. The digital interface 7 thus corresponds to the control unit 7 of FIG. 1 and acts as a controller in a closed feedback control loop.

The possibility of feedback and feedback control exists in all embodiments of the apparatus 1 in accordance with the invention, but is no longer shown in the following drawings for reasons of simplicity. For the same reason, the optional filter and/or amplifier stage 5 (see FIG. 1) is also not shown in the FIGS. 2 to 9.

Figure 3:
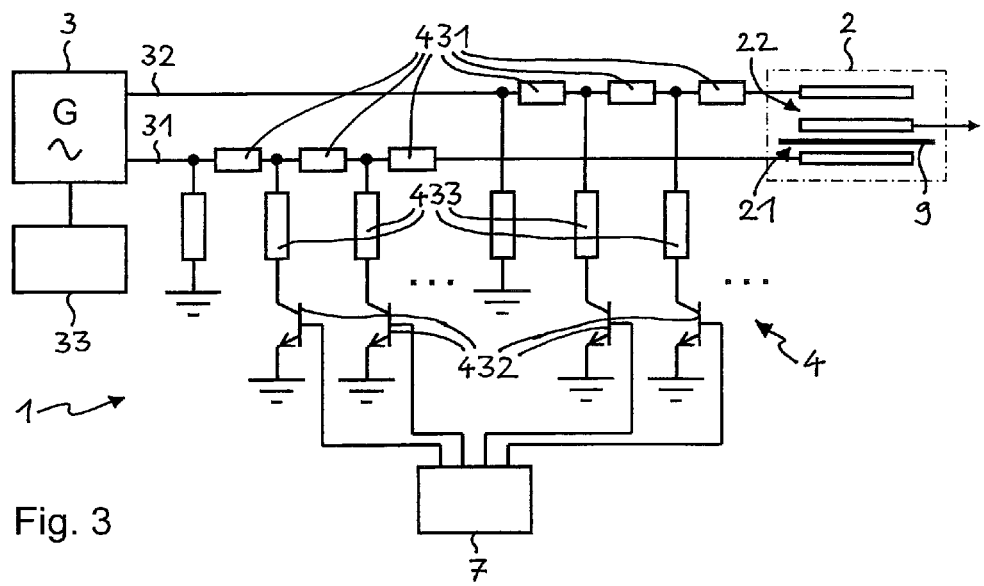

FIG. 3 shows a second embodiment of the apparatus 1 in accordance with the invention. In this case, the balancing means 4 are arranged as resistive conductors. Such resistive conductors substantially contain a plurality of series-connected resistors 431 which can be activated or deactivated individually or in groups by switches 432 via further resistors 433. A balancing of the apparatus 1 can be achieved by suitable switch positions which can be controlled on their part by a digital interface 7.

Figure 4:
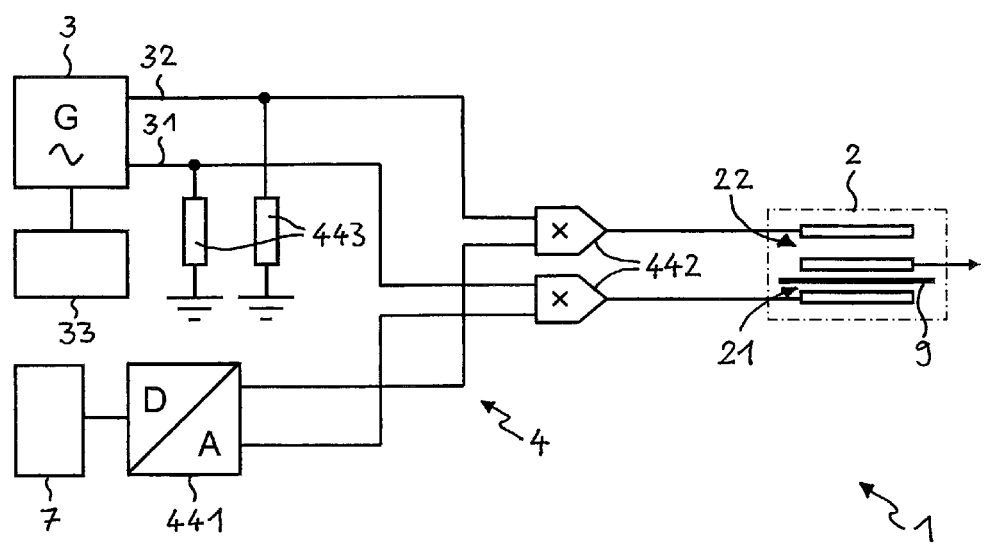

In a third embodiment of the apparatus 1 in accordance with the invention according to FIG. 4, a differential digital-to-analog converter 441 with two outputs of arbitrary bit-width is used. The digital-to-analog converter 441 is controlled by a suitable digital interface 7. It generates a voltage which is proportional to the detuning or balancing of the measuring circuit 2. The alternating voltage of the synthesizer 3 is modulated with this voltage in an analog mixer or multiplier 442, and the signal thus modulated is applied to the measuring circuit 2. The amplitude of the alternating voltage generated by the synthesizer 3 can thus be set at will until the apparatus 1 is balanced. The two resistors 443 shown in FIG. 4 are used for converting an alternating current supplied by the synthesizer 3 into an alternating voltage. They can be omitted when the synthesizer 3 is already arranged as an alternating voltage source. Two single-pole digital-to-analog converters could be used instead of the differential digital-to-analog converter 441.

Figure 5:
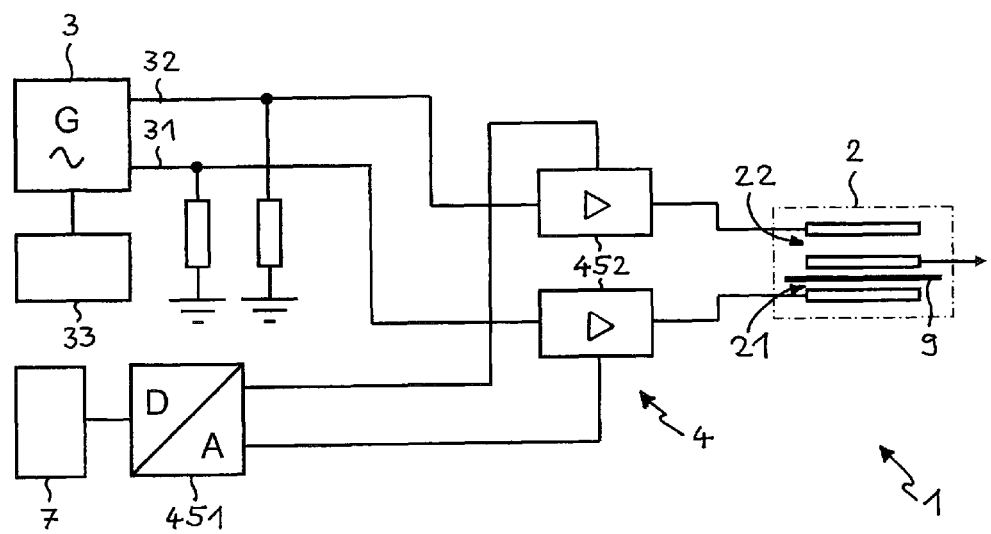

A fourth embodiment of the apparatus 1 in accordance with the invention as shown in FIG. 5 works according to the principle of the voltage-controlled amplifier. It contains two voltage-controlled variable amplifiers 452 (variable gain amplifiers, VGA) for the two output signals of the synthesizer 3. The gains of the variable gain amplifier 452 are controlled for example by a digital-to-analog converter 451, which on its part is controlled by the digital interface 7. A balancing of the apparatus 1 can be achieved by setting suitable gains for the two output signals of the synthesizer 3.

Figure 6:
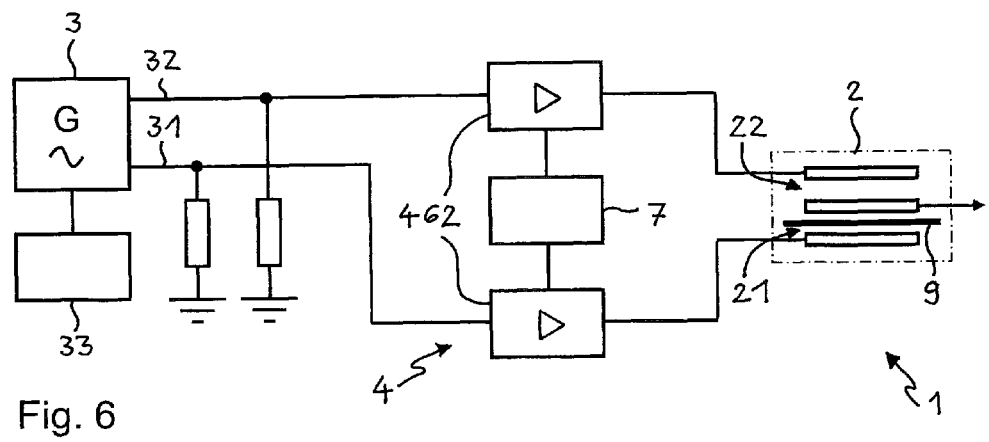

A fifth embodiment of the apparatus 1 in accordance with the invention, which is shown in FIG. 6, works analogously to the embodiment of FIG. 5. Amplifiers 462 with programmable gain (programmable gain amplifiers, PGA) are used instead of the analog controlled variable gain amplifiers 452. They are triggered by a suitable digital interface 7. The digital-to-analog converter 451 can be omitted in this embodiment.

Figure 7:
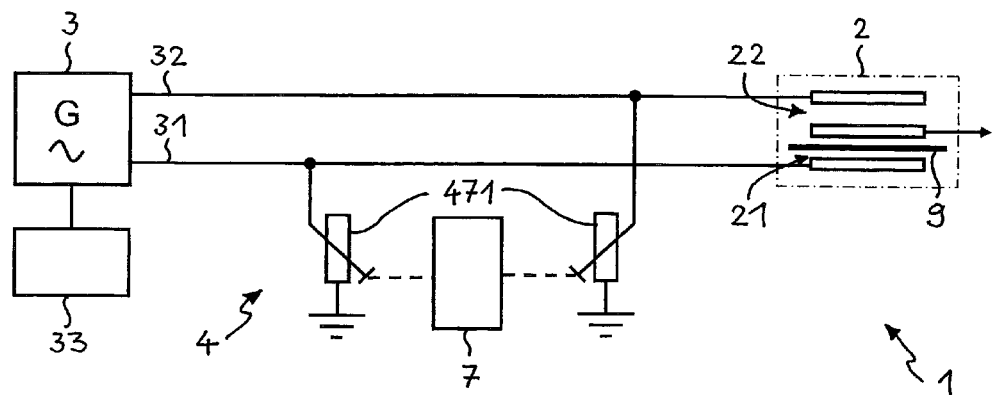

A sixth embodiment of the apparatus 1 in accordance with the invention according to FIG. 7 uses digital potentiometers or rejustors 471. They can be triggered via one or two digital interfaces 7, so that their resistances are changed in such a way that a purposeful voltage drop is produced by the alternating current generated by the synthesizer 3. If the synthesizer 3 is arranged as an alternating voltage source, the apparatus 1 can alternatively be wired as a voltage divider.

Figure 8:
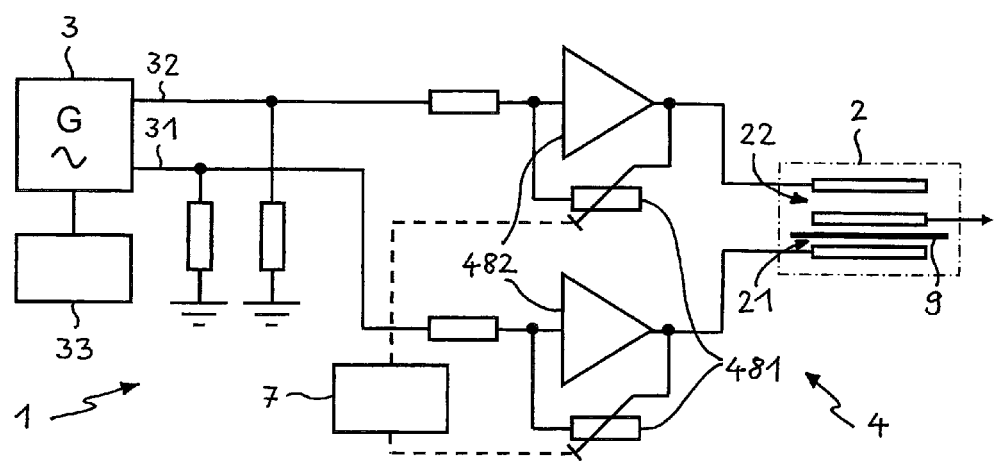

Digital potentiometers or rejustors 481 are also used in a seventh embodiment of the apparatus 1 in accordance with the invention as shown in FIG. 8, namely for example in each case in negative feedback of an amplifier 482 which amplifies an alternating signal generated by the synthesizer 3 between the synthesizer 3 and the measuring circuit 2.

In the embodiment of FIGS. 7 and 8, analog potentiometers could be used instead of the digital potentiometers 481. An operator could manually balance the apparatus 1 with them.

Figure 9:
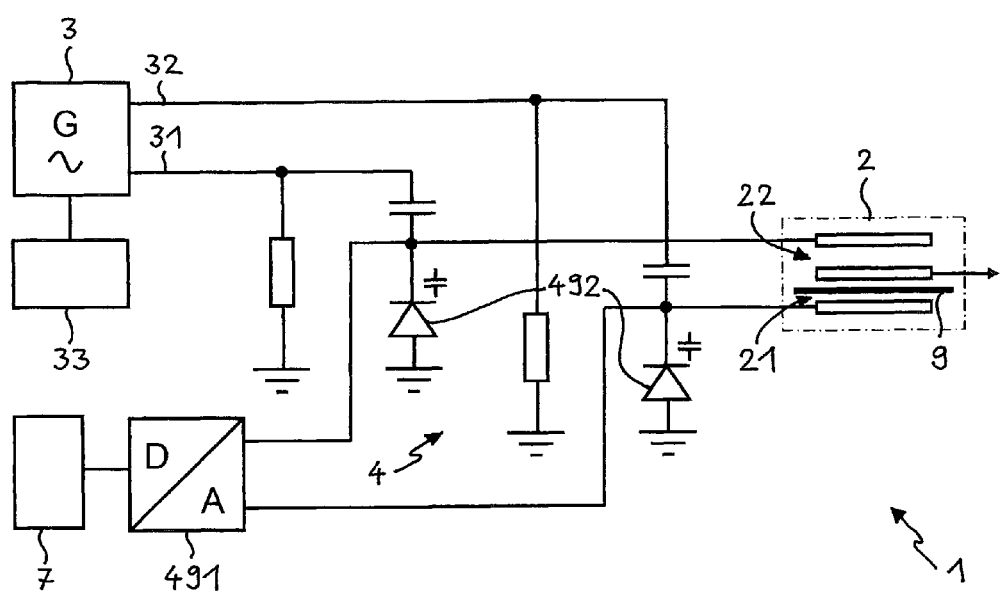

In an eighth embodiment of the apparatus 1 in accordance with the invention according to FIG. 9, the capacitive voltage dividers are formed with variable-capacitance diodes 492. The voltages for the control of the variable-capacitance diodes 492 are supplied for example by a differential digital-to-analog converter 491 with two outputs, which on its part is controlled by a digital interface 7. Two single-pole digital-toanalog converters could be used as an alternative to the differential digital-to-analog converter 491.

It is understood that the present invention is not limited to the embodiments discussed above. With the knowledge of the invention, the person skilled in the art will be able to derive further variants which also belong to the subject matter of the present invention. Such variants can be combinations of the embodiments as discussed above for example. The person skilled in the art has knowledge of many electrical components which can be used as balancing means 4 for the apparatus 1 in accordance with the invention.

List of Reference Numerals

1 Apparatus
2 Measuring circuit
21 Capacitance to be measured, measuring capacitor
22 Reference capacitor
3 Alternating signal generator
31, 32 Outputs of the alternating signal generator
33 Digital interface for triggering the alternating signal generator
4 Balancing means
411 Digital-to-analog converter
421 Resistors
422 Switch
431, 433 Resistors
432 Switch
441 Digital-to-analog converter
442 Multiplier
451 Digital-to-analog converter
452 Variable amplifier
462 Amplifier with variable amplification
471 Digital potentiometer or rejustor
481 Digital potentiometer or rejustor
482 Amplifier
491 Digital-to-analog converter
492 Variable-capacitance diode
5 Filter and/or amplifier stage
6 Evaluation circuit
7 Control unit
9 Test subject

The invention claimed is:

1. A method for the symmetric balancing of an apparatus for the capacitive examination of a moved elongated textile test material by means of a capacitor arrangement:
the apparatus comprising,
a measuring circuit comprising the capacitor arrangement and a reference capacitor which is connected to the capacitor arrangement,
at least one alternating signal generator for applying an electric alternating signal to the capacitor arrangement,
an evaluation circuit for evaluating at least one electric measuring quantity of an electric signal tapped from a first side of the capacitor arrangement,
a balancing apparatus disposed in an electric path between the at least one alternating signal generator and a second side of the capacitor arrangement, by which at least one parameter of the electric alternating signal is changeable such that an output signal of the evaluation circuit assumes a value of zero under defined constant conditions, and
a control apparatus for emitting an electric control signal to the balancing apparatus, by which the change of the at least one parameter is controllable, the method comprising, the capacitor arrangement without test material is left temporally substantially unchanged,
an electric alternating signal is generated by the at least one alternating signal generator and applied to the capacitor arrangement,
an electric output signal is tapped from the capacitor arrangement,
at least one electric measuring quantity of the electric output signal tapped from the capacitor arrangement is evaluated by the evaluation circuit,
at least one parameter of the electric alternating signal is changed in the electric path between the at least one alternating signal generator and the measuring circuit by the balancing apparatus such that an output signal of the evaluation circuit assumes a value of zero under defined constant conditions,
the change of the at least one parameter is controlled by the control apparatus by means of the electric control signal, and
the electric control signal is influenced by the output signal.

2. The method according to claim 1, wherein the influence on the electric control signal by the output signal occurs automatically in a closed feedback control loop.

3. The method according to claim 1, wherein the apparatus comprises a feedback, by which an output signal of the capacitor arrangement or the evaluation circuit acts upon the control apparatus.

4. The method according to claim 1, wherein the balancing apparatus contains a plurality of electric resistors that are selectively activated and deactivated individually or in groups.

5. The method according to claim 1, wherein the balancing apparatus contains a modulator for an amplitude modulation of the electric alternating signal.

6. The method according to claim 1, wherein the balancing apparatus contains an amplifier with variable or programmable gain for amplifying the electric alternating signal.

7. The method according to claim 1, wherein the balancing apparatus contains a digital potentiometer or a rejustor.

8. The method according to claim 1, wherein the balancing apparatus contains a variable-capacitance diode.

9. A method for testing of at least one of an apparatus and components connected downstream from an apparatus for determining at least one dielectric property of a capacitor arrangement:
the apparatus comprising,
a measuring circuit comprising the capacitor arrangement and a reference capacitor which is connected to the capacitor arrangement,
at least one alternating signal generator for applying an electric alternating signal to the capacitor arrangement,
an evaluation circuit for evaluating at least one electric measuring quantity of an electric signal tapped from the capacitor arrangement,
a balancing apparatus that is arranged in an electric path between the at least one alternating signal generator and the measuring circuit, by which at least one parameter of the electric alternating signal is changeable such that an output signal of the evaluation circuit assumes a value of zero under defined constant conditions, and
a control apparatus for emitting an electric control signal to the balancing apparatus, by which the change of the at least one parameter is controllable,
the method comprising, the capacitor arrangement is essentially left in a temporally unchanged way, an electric alternating signal is generated by the at least one alternating signal generator and is applied to the capacitor arrangement, at least one electric measuring quantity of an electric signal tapped from the capacitor arrangement is evaluated, the at least one parameter of the electric alternating signal is changed in the electric path between the at least one alternating signal generator and the measuring circuit by the balancing apparatus, the change of the at least one parameter is controlled by the electric control signal emitted by the control apparatus, and the electric control signal is independent of an output signal of the capacitor arrangement, and is temporally rapidly changing and at least one of synthetically generated and previously stored.

10. The method according to claim 9, wherein the capacitor arrangement is decoupled from the alternating signal generator such that it does not relevantly influence the basic frequency and the signal shape of the applied alternating signal.

11. The method according to claim 9, wherein the balancing apparatus contains a plurality of electric resistors which can be activated and deactivated individually or in groups.

12. The method according to claim 9, wherein the balancing apparatus contains a modulator for an amplitude modulation of the electric alternating signal.

13. The method according to claim 9, wherein the balancing apparatus contains an amplifier with variable or programmable gain for amplifying the electric alternating signal.

14. The method according to claim 9, wherein the balancing apparatus contains a digital potentiometer or a rejustor.

15. The method according to claim 9, wherein the balancing apparatus contains a variable-capacitance diode.

16. The method according to claim 9, wherein the apparatus contains a reference capacitor that is connected in series to the capacitor arrangement.

17. The method according to claim 16, wherein the at least one alternating signal generator is configured to apply two electric alternating voltages with opposite phases to the capacitor arrangement and the reference capacitor, respectively.

18. The method according to claim 17, wherein the balancing apparatus is disposed in in at least one of (1) the electric path between the alternating signal generator and the capacitor arrangement and (2) the electric path between the at least one alternating signal generator and the reference capacitor.

19. An apparatus for determining at least one dielectric property of a capacitor arrangement, comprising:

an evaluation circuit for evaluating at least one electric measuring quantity of an electric signal tapped from a first side of the capacitor arrangement, a measuring circuit comprising the capacitor arrangement and a reference capacitor which is connected in series to the capacitor arrangement, at least one alternating signal generator for applying two electric alternating voltages with opposite phases to the capacitor arrangement and the reference capacitor, respectively, a balancing apparatus arranged in an electric path between the at least one alternating signal generator and a second side of the capacitor arrangement, by which at least one parameter of the electric alternating signal is changeable such that an output signal of the evaluation circuit assumes the value zero under defined constant conditions, and a control apparatus for emitting an electric control signal to the balancing apparatus, by which the change of the at least one parameter is controllable.

20. The apparatus according to claim 19, wherein the apparatus comprises a feedback, by which an output signal of the capacitor arrangement or the evaluation circuit acts upon the control apparatus.

21. The apparatus according to claim 19, wherein the capacitor arrangement is decoupled from the alternating signal generator such that it does not relevantly influence the basic frequency and the signal shape of the applied alternating signal.

22. The apparatus according to claim 19, wherein the balancing apparatus contains a plurality of electric resistors that are selectively activated and deactivated individually or in groups.

23. The apparatus according to claim 19, wherein the balancing apparatus contains a modulator for an amplitude modulation of the electric alternating signal.

24. The apparatus according to claim 19, wherein the balancing apparatus contains an amplifier with at least one of variable gain and programmable gain for amplifying the electric alternating signal.

25. The apparatus according to claim 19, wherein the balancing apparatus contains at least one of a digital potentiometer and a rejustor.

26. The apparatus according to claim 19, wherein the balancing apparatus contains a variable-capacitance diode.

27. The apparatus according to claim 26, wherein the balancing apparatus is disposed in at least one of (1) the electric path between the alternating signal generator and the capacitor arrangement and (2) the electric path between the at least one alternating signal generator and the reference capacitor.

* * * * *